United States Patent [19]

Anthony

[11] Patent Number: 4,464,114
[45] Date of Patent: Aug. 7, 1984

[54] SURGICAL PACK RETENTION DEVICE

[76] Inventor: Albert J. Anthony, 45 Central St., W. Boylston, Mass. 01583

[21] Appl. No.: 458,298

[22] Filed: Jan. 17, 1983

Related U.S. Application Data

[63] Continuation of Ser. No. 291,445, Aug. 10, 1981, abandoned.

[51] Int. Cl.³ .............................................. A61C 19/06
[52] U.S. Cl. ................................................... 433/229
[58] Field of Search ........................ 433/229, 215, 80; 128/260, 325, 326; 604/1

[56] References Cited

U.S. PATENT DOCUMENTS

| | | | |
|---|---|---|---|
| 1,010,146 | 11/1911 | Ivory | 433/136 |
| 1,730,266 | 10/1929 | Daily | 433/136 |
| 2,551,374 | 5/1951 | Hansen | 24/259 R |
| 4,020,558 | 5/1977 | Cournut et al. | 433/80 |

Primary Examiner—Robert Peshock
Attorney, Agent, or Firm—Blodgett & Blodgett

[57] ABSTRACT

An oral pack retention system for use in covering a location in the mouth and including a retention fixture, a flexible wire and a mass of moldable pack material. The retention fixture has a central portion which is adapted to be along the side of the tooth and a pair of spaced arms which extend away from the central portion to define an opening and to be anchored in the mass. The flexible wire is adapted to extend around the tooth and to be fastened to the central portion of the fixture. The mass of moldable material is molded to the fixture so that it covers the location in the mouth.

4 Claims, 3 Drawing Figures

SURGICAL PACK RETENTION DEVICE

This is a continuation of application Ser. No. 291,445 filed Aug. 10, 1981, now abandoned.

BACKGROUND OF THE INVENTION

After a dentist has performed one of a variety of types of surgery in the mouth of a patient, it is necessary to protect the surgical site. For that purpose, it is common practice to use a so-called "pack" in the form of an elastomer plastic. Unfortunately, for one reason or another, it is difficult to maintain the pack in place and they tend to become loosened, lost prematurely, and sometimes even swallowed. If this occurs, the surgerized tissue is not protected and the trauma may cause pain, hemmorhage, or susceptibility to infection. A particularly important use for the pack is in the case of the free gingival graft where it is difficult to retain the pack on the donor site and the palate. In that case, it is particularly important to protect the site from which the tissue surface has been removed. Prior to the present invention the only method of pack retention with any efficiency at all was the "surgical stent" which is a custom-made appliance. These appliances are very time consuming and expensive to make and are less confortable to the patient. For these reasons, they are not usually constructed unless very extensive donor sites require dressing (surgical pack). The stent can easily be too lose or too tight, resulting in the loss of the stent and pack. The stent also often allows liquids to seep to the raw tissue causing sever pain. Attempts have been made in the past to provide a means of holding the pack in place, but they have been less than successful, particularly when the wound was located in the palate. These and other difficulties experienced with the prior art devices have been obviated in a novel manner by the present invention.

It is, therefore, an outstanding object of the invention to provide a surgical pack retention device to maintain a surgical pack securely in place.

Another object of this invention is the provision of an appliance for periodontal surgical use, where the wound is located on the palate.

A further object of the present invention is the provision of a surgical pack retention device that is adaptable to all positions in the mouth irrespective of the shape, nature, or location of the tooth.

It is another object of the instant invention to provide a periodontal appliance which is simple and rugged in construction, which can be readily manufactured from easily obtainable materials, and which is capable of being sterilized either by autoclave or high dry heat.

It is another object of the instant invention to provide a periodontal appliance which is inexpensive to manufacture and which can be easily applied to either large or small surgical sites.

With these and other objects in view, as will be apparent to those skilled in the art, the invention resides in the combination of parts set forth in the specification and covered by the claims appended hereto.

SUMMARY OF THE INVENTION

In general, the invention consists of a surgical pack retention device for use in maintaining a surgical pack in place and having a retention fixture adapted to be located adjacent a tooth. A flexible wire is provided to extend tightly around the tooth and to be fastened to the fixture.

Specifically, the fixture has an extruded shape and both the fixture and the wire are formed of stainless steel.

BRIEF DESCRIPTION OF THE DRAWINGS

The character of the invention, however, may be best understood by reference to one of its structural forms, as illustrated by the accompanying drawings, in which.

DESCRIPTION OF THE PREFERRED EMBODIMENT

Figure 1:
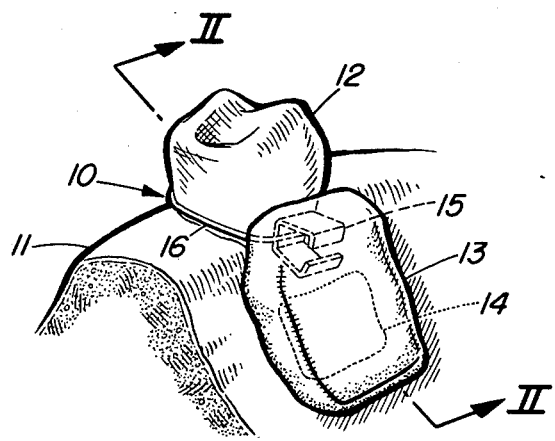
FIG. 1 is a perspective view of a surgical pack retention device incorporating the principles of the present invention.

Referring first to FIG. 1, wherein are best shown the general features of the invention, the surgical pack retention device, indicated generally by the reference numeral 10, is shown in use in a patient's mouth, having a palatal tissue surface 11 and a tooth 12. The device is shown in use in holding a surgical pack 13 over a surgical donor site 14 on the palate 11.

Figure 2:
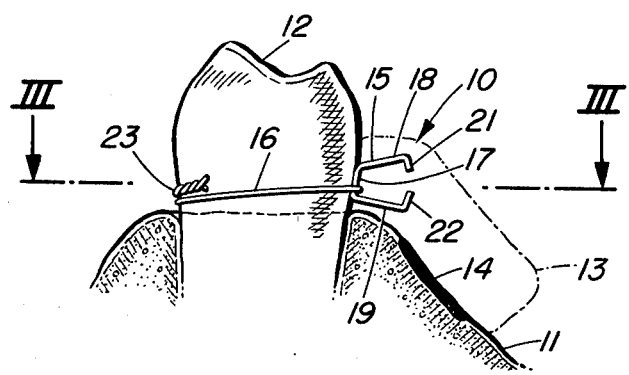
FIG. 2 is a vertical sectional view of the device taken on the line II—II of FIG. 1.
Figure 3:
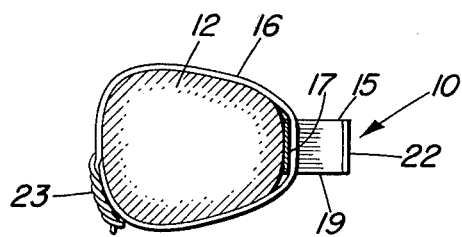
FIG. 3 is a plan view of the device as viewed on the line III—III of FIG. 2.

FIGS. 2 and 3 show the details of the surgical pack retention device 10 which has a retention device 15 located adjacent the tooth 12. The device is provided with a wire 16 which extends tightly around the tooth and is fastened to the fixture 15. As is evident in FIG. 2, the fixture 15 has an extruded shape, that is to say, it has a constant cross-section. The wire 16 and the fixture 15 are formed of a non-corrosive material such as stainless steel. The fixture 15 has a flat central portion 17 which lies against the tooth and which is fastened to the wire 16 by welding or the like. The fixture 15 is also provided with arms 18 and 19 which extend laterally away from the central portion 17 at the top and bottom, respectively. These arms extend at an obtuse angle to the central portion. The outer end of the upper arm 18 is provided with a downwardly-extending flange 21, while a similar flange 22 extends upwardly from the outer end of the lower arm 19. The flanges, therefore, extend toward one another to the extent that they each occupy approximately one-third of the space between the ends of the arms.

The method of operation and the advantages of the present invention will now be readily understood in view of the above description. When the surgery (especially a free gingival graft) has been completed, the result is a raw connective tissue area without the normal epithelial covering at the site 14. When the surgery has been completed, it is necessary to apply the pack 14 to protect it and assist in healing. For that purpose, the fixture 15 with the wire 16 attached, is placed against the inner surface of the tooth 12 at a location which is close to where the tooth emerges from the gingiva 11. The ends of the wire 16 are carried around to the outer side of the tooth where they are twisted together to form the portion 23. The portion 23 is then bent back toward the tooth to lie flat against it, so that it does not irritate the portion of the cheek which lies opposite it and would otherwise contact it. The pack 13 is then molded around and within the fixture 15, so that it extends over the site 14. The apparatus holds the pack securely in this way and it is not easily dislodged. This particular manner of holding the surgical pack 13 is particularly adaptable in the case of the free gingival graft, wherein the site 14 is a "donor" site. The invention, therefore, serves the purpose of retaining a periodontal or surgical pack or dressing in the oral cavity subsequent to various types of surgery, especially periodontal surgery. The fixture is anchored firmly to the tooth. The surgical pack material is molded around and within the fixture and against the surface of the tooth to which it is anchored and against adjacent teeth. The pack covers the surgical site and is then allowed to set. This is especially useful at the donor site of a gingival graft which would be on the palate where it is extremely difficult to maintain a pack. The well-retained pack gives post-operative comfort to the patient, protects the tissue from trauma and irritation, and prevents hemmorhage during early healing.

It is obvious that minor changes may be made in the form and construction of the invention without departing from the material spirit thereof. It is not, however, desired to confine the invention to the exact form herein shown and described, but it is desired to include all such as properly come within the scope claimed.

The invention having been thus described, what is claimed as new and desired to secure by Letters Patent is:

1. An oral pack retention system for use in covering a location in the mouth, comprising:
   (a) a retention fixture adapted to be located against the side surface of a tooth, said fixture having a central portion which is adapted to lie along the side surface of the tooth and a pair of spaced arms extending away from the central portion and terminating in free ends which define an opening which is spaced from said central portion and said tooth surface,
   (b) a flexible wire adapted to extend tightly around the tooth and to be fastened to the central portion of the fixture, and
   (c) a mass of moldable pack material molded to the fixture so that it covers said location and engulfs said fixture, so that said fixture is effectively anchored within said mass.

2. An oral pack retention system as recited in claim 1, wherein the fixture has an extruded shape, and wherein the fixture and the wire are formed of a corrosion-resistant material.

3. An oral pack retention system as recited in claim 2, wherein the fixture is formed of stainless steel and is attached by welding to the wire.

4. An oral pack retention system as recited in claim 1, wherein each arm lies at an obtuse angle to the central portion, and a flange extends from the end of each arm toward each other.

* * * * *